United States Patent
Celia

(10) Patent No.: US 10,259,914 B2
(45) Date of Patent: Apr. 16, 2019

(54) COSMETIC SPONGE AND METHOD FOR PROVIDING A COSMETIC SPONGE

(71) Applicant: Wayne Celia, Woonsocket, RI (US)

(72) Inventor: Wayne Celia, Woonsocket, RI (US)

(73) Assignee: Diversified Global Technologies, LLC, Woonsocket, RI (US)

( * ) Notice: Subject to any disclaimer, the term of this patent is extended or adjusted under 35 U.S.C. 154(b) by 0 days.

(21) Appl. No.: 15/189,184

(22) Filed: Jun. 22, 2016

(65) Prior Publication Data

US 2018/0237592 A1 Aug. 23, 2018

Related U.S. Application Data

(62) Division of application No. 13/633,605, filed on Oct. 2, 2012, now Pat. No. 9,403,953.

(51) Int. Cl.
| | |
|---|---|
| *C08H 1/06* | (2006.01) |
| *C08J 9/00* | (2006.01) |
| *C07K 14/78* | (2006.01) |
| *C08L 89/06* | (2006.01) |
| *A61Q 19/00* | (2006.01) |
| *A61K 8/02* | (2006.01) |
| *B29C 44/02* | (2006.01) |
| *B29K 75/00* | (2006.01) |
| *B29K 105/04* | (2006.01) |

(52) U.S. Cl.
CPC ............. *C08H 1/06* (2013.01); *A61K 8/0208* (2013.01); *A61Q 19/00* (2013.01); *B29C 44/02* (2013.01); *C07K 14/78* (2013.01); *C08J 9/0085* (2013.01); *C08L 89/06* (2013.01); *A61K 2800/10* (2013.01); *B29K 2075/00* (2013.01); *B29K 2105/04* (2013.01); *B29K 2995/0092* (2013.01); *C08J 2375/04* (2013.01); *C08J 2489/00* (2013.01)

(58) Field of Classification Search
None
See application file for complete search history.

(56) References Cited

U.S. PATENT DOCUMENTS 6,566,576 B1 * 5/2003 Komerska ......... A61F 13/00063
602/43
2007/0253912 A1 * 11/2007 Furlan ................... A61K 8/65
424/45

\* cited by examiner

*Primary Examiner* — Melissa L Fisher
(74) *Attorney, Agent, or Firm* — IP Attorneys Group, LLC

(57) ABSTRACT

This invention relates to a cosmetic sponge and a method of providing a cosmetic sponge incorporating a non-denatured collagen and other additives for skin care, cleaning, and cosmetic application.

20 Claims, 5 Drawing Sheets

COSMETIC SPONGE AND METHOD FOR PROVIDING A COSMETIC SPONGE

CROSS REFERENCE TO CO-PENDING APPLICATIONS

This application is a divisional of and claims priority to U.S. application Ser. No. 13/633,615 filed on Oct. 2, 2012 and titled "Cosmetic Sponge and Method for Providing a Cosmetic Sponge," which is a continuation-in-part of and claims priority to U.S. application Ser. No. 13/176,841 filed on Jul. 6, 2011 and titled "Footbed with Non-Denatured Collagen." The contents of these above-referenced applications are relied upon and are incorporated herein by reference in their entireties.

FIELD OF INVENTION

The invention relates to a cosmetic sponge, and more particularly to a polymer foam sponge containing a non-denatured collagen.

BACKGROUND OF INVENTION

Collagen is a general term describing a variety of naturally occurring proteins found in animals, especially in the flesh and connective tissues, It is considered to be the most abundant protein in mammals, comprising 25% to 35% of the whole body protein.

The most abundant form of collagen is believed to be Type I collagen, which is found in skin, tendons, vascular ligature, organ, and bones. Type I collagen appears to comprise over 90% of the total collagen in the body. The commonly accepted model characterizes type I collagen as a fibrillar form of collagen, composed of three polypeptide strands in a triple helix. The triple helices are further associated into coiled coils, which are associated further into super coils referred to as collagen, microfibrils, These microfibrils are interdigitated with other microfibrils, forming collagen fibrils which can be so well ordered as to be crystalline in some respects.

Isolated collagen has many uses, and a wide variety of techniques have been developed to isolate the collagen. These techniques can have very different effects on the structure of the collagen, and on the form which is isolated. Treatment with strong acids and bases can hydrolyze the cross-links and other intermolecular structures which hold the polypeptide strands to each other, generating the viscous, water-soluble form of collagen known as gelatin. Cioca et al appears to teach treatment with enzymes such as casein to isolate forms of collagen for the manufacture of artificial chamois (Cioca et al, U.S. Pat. No. 4,327,195, 1982). Acid extraction of calf tendons has been proposed to prepare a biocompatible fluid containing acid-soluble collagen for injection. (Kemp et al, U.S. Pat. No. 5,106,949, 1992). These preparations of soluble collagens would be expected to denature the collagen, resulting in the disruption of the intermolecular bonding and of the fibril and microfibril structure of the collagen.

Insoluble forms of collagen I are typically produced by mechanical methods which avoid disruption of the intermolecular collagen bonding. One method proposed is a combination of simple cutting and grinding processes (eg Aceto et al, U.S. Pat. No. 3,665,998, 1972), and the resulting particulate collagen may be formed into structures by, for example, suspension and freeze-drying (eg Cioca, U.S. Pat. No. 4,412,947, 1983).

When refined to a small enough particle size, it has been reported that the natural structure of even "insoluble" collagen may be reduced to the point that it exhibits some solubility in strong solvents such as dimethyl sulfoxide and dimethyl formamide. In many cases, these materials can also be handled in water dispersions. The use of very small particles of lower molecular weight collagens (less than 0.5 millimeter particles for molecular weights less than 30,000, for example) has been reported to improve the properties of hydrophobic polyurethane foams when used as a filler material. (Cioca et al, U.S. Pat. No. 4,327,195, 1985). Processing of the collagen to the extent required for this type of handling, however, may denature it to the point that the natural elasticity, flexibility, strength and stability of the collagen fibers is reduced.

In light of the number of techniques for processing collagen which denature the protein, the advantages of a clean, non-denatured collagen in combination with a polymer foam have yet to be realized. There is still a need, therefore, for a sponge that incorporates non-denatured collagen fibers.

Collagen has been used in cosmetics applications both intradermally (by injection) and extradermally (by application to the surface of the skin). Reportedly, one of the mechanisms of the visible appearance of skin aging is the loss of collagen, resulting in a reduction of the soft tissue and formation of wrinkles. Injectable collagen compositions (eg Janzen et al, U.S. Pat. No. 5,523,291, 1996) have been proposed for soft tissue augmentation, to reduce visible wrinkling in aging skin or to reduce the appearance of scarring, and to augment features such as lips and cheeks. Cosmetic creams may contain hydrolyzed collagen for use as moisturizers or to reduce the visible appearance of wrinkles and lines. Other skin treatments, including pastes and foils (eg Bremer et al, U.S. Pat. No. 4,131,650, 1978) may include soluble collagen in a form which can be transported to and absorbed by the skin. The lack of a fibrillar structure in these hydrolyzed collagen products, however, typically results in reabsorption of the collagen into the body and destruction by collagenase, requiring frequent reapplication of the treatments.

There is also a need, therefore, for a non-hydrolyzed, non-denatured collagen which can be applied extradermally, and for a convenient form in which to apply that material.

What is desired is a cosmetic sponge and a method for providing a cosmetic sponge that benefits from the properties imparted from the incorporation of a non-denatured collagen, and for a cosmetic sponge that can apply a beneficial form of non-denatured collagen to the skin.

SUMMARY OF INVENTION

It is therefore an object of the invention to provide a cosmetic sponge containing a non-denatured collagen. In one embodiment, this cosmetic sponge comprises a polymer foam, non-denatured collagen, and at least one additive. In one embodiment, this non-denatured collagen is formed by carefully controlling the pH and amount of heat to which the collagen is exposed during the extraction process. By avoiding extremes of pH and heat, the denaturation, or loss of natural structure, of the collagen is avoided or at least minimized. In one embodiment, the non-denatured collagen is prepared under pH conditions ranging from approximately 13 to approximately 3. In another embodiment, the non-denatured collagen is prepared under pH conditions ranging from approximately 10 to approximately 4. In yet another embodiment the non-denatured collagen is prepared under pH conditions ranging from approximately 8 to approximately 5. In one embodiment, the non-denatured collagen has a fiber length of less than approximately 10 mm.

In some embodiments, the additives are selected from a group consisting of: skin care agents, hydrocolloid absorptive agents, medicaments, proteins, enzymes, nucleic acids, vitamins, soaps, hemostatic agents, antibacterial agents, antifungal agents, surfactants, pH buffers, mineral salts, trace elements, plant extracts, animal extracts, disinfecting and sterilizing agents, and combinations thereof.

In some embodiments, the cosmetic sponge further comprises a superabsorbent polymer.

In some embodiments, the invention comprises the reaction product of a mixture containing a predetermined amount of non-denatured collagen, a predetermined amount of a prepolymer, and at least one additive. In one embodiment, the additive or additives are selected from the group consisting of skin care agents, hydrocolloid absorptive agents, medicaments, proteins, enzymes, nucleic acids, vitamins, soaps, hemostatic agents, antibacterial agents, antifungal agents, surfactants pH buffers, mineral salts, trace elements, plant extracts, animal extracts, disinfecting and sterilizing agents, and combinations thereof. In one embodiment, the mixture also contains a superabsorbent polymer.

A second object of the invention is to provide a method for making a cosmetic sponge. In some embodiments, this method comprises the steps of: forming a mixture having at least a predetermined amount of non-denatured collagen and water, and mixing a predetermined amount of a prepolymer with said mixture to form a foam layer. In some embodiments, the method further comprises the steps of adding an agent from the group consisting of a cross-linking agent, a catalyst, a surfactant, or combinations thereof. In some embodiments, the method further comprises the step of adding at least one additive from the group consisting of skin care agents, hydrocolloid absorptive agents, medicaments, proteins, enzymes, nucleic acids, vitamins, soaps, hemostatic agents, antibacterial agents, antifungal agents, surfactants, pH buffers, mineral salts, trace elements, plant extracts animal extracts, disinfecting and sterilizing agents and combinations thereof.

In some embodiments, the method further comprises the steps of depositing the mixture on releasable bottom paper disposed on a movable carrier; covering the upper surface of the mixture with releasable top paper as the aqueous mixture is moved with the movable carrier; advancing the foam layer in the top and bottom release paper by moving the carrier; sizing the foam layer to the desired thickness removing the top and bottom releasable paper; and drying the sized cosmetic sponge to remove moisture.

A further object of the invention is to provide a layered composite material for use as a cosmetic sponge. In some embodiments, this material comprises a cover layer and a foam layer, wherein the foam layer is comprised of a polymer foam, a non-denatured collagen, and at least one additive, and wherein a first surface of said foam layer is in contact with said cover layer. In one embodiment, the foam layer is hydrophilic with respect to said cover layer. In some embodiments, the cover layer comprises a material selected from the group consisting of a randomized polyester fiber material, a sock liner material, a non-woven material, a non-woven fiber-web, and a felted non-woven fiber web. In some embodiments the layered composite material comprises a third layer bonded to a second surface of said foam layer.

BRIEF DESCRIPTION OF FIGURES

The features of the invention believed to be novel and the elements characteristic of the invention are set forth with particularity in the claims. The figures are for illustration purposes only and are not drawn to scale. The invention itself, however, both as to organization and method of operation, may be understood by reference to the detailed description which follows taken in conjunction with the accompanying drawings in which the drawings show typical embodiments of the invention and are not intended to be limited of its scope.

DETAILED DESCRIPTION

Figure 1:
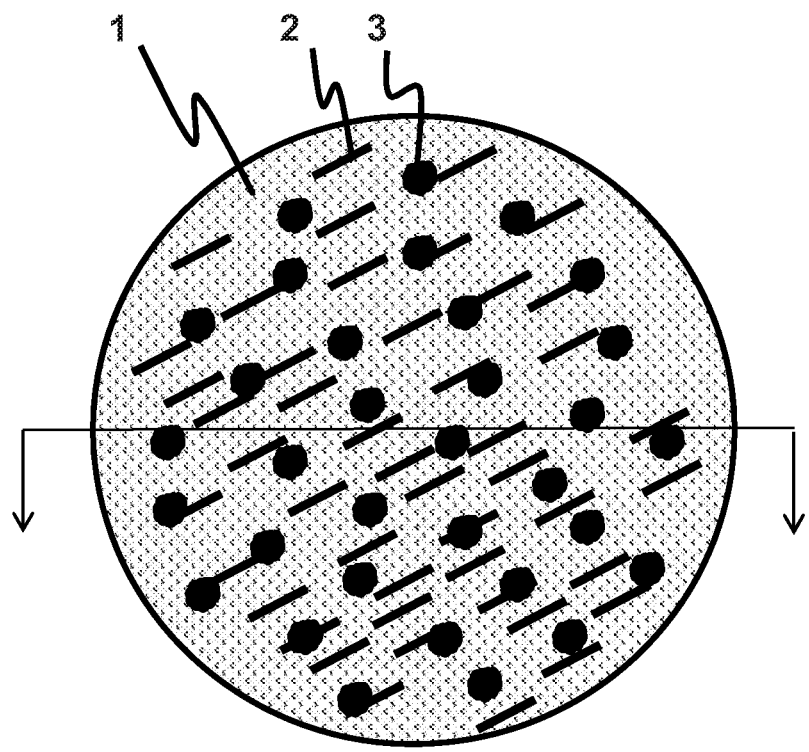
FIG. 1 depicts one embodiment of a cosmetic sponge in accordance with the present invention.
Figure 1A:
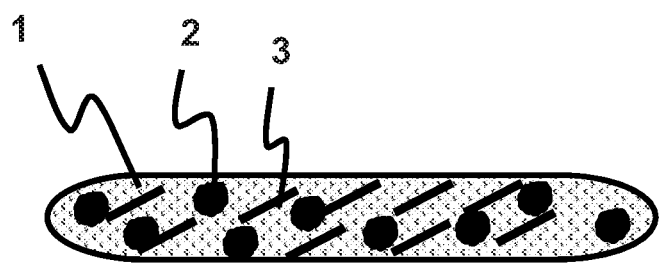
FIG. 1a depicts the same embodiment in cutaway view, to show the internal structure of the sponge.

FIGS. 1 and 1a depict one embodiment of this invention, a cosmetic sponge comprising a polymer foam (1) containing a non-denatured collagen (2) and at least one additive (3) dispersed throughout. The nature and preparation of the polymer foams in this invention reflect in part the teachings with regard to hydrophilic polyurethane foams of U.S. Pat. Nos. 5,976,616, 6,706,775, and 6,566,576, hereby incorporated by reference in their entirety.

In some embodiments of this invention, the polymer foam is prepared by polymerization of an aqueous prepolymer mixture. In one embodiment, the aqueous prepolymer mixture comprises adequate water, a predetermined amount of a hydrophilic urethane prepolymer, a predetermined amount of non-denatured collagen, and, at least one additive. In some embodiments, the cosmetic sponge of the invention contains the reaction product of a mixture comprising a predetermined amount of a non-denatured collagen, a predetermined amount of a prepolymer, and at least one additive.

In some embodiments, one or more additional components are added to modify the properties of the resulting foam. In various embodiments, these components include dispersants to ensure that the at least one additive and the non-denatured collagen are adequately dispersed throughout the foam; surfactants to modify the hydrophilicity of the resulting polymer foam foaming and blowing agents to modify the number, size, and uniformity of the cells in the resulting foam. Other components which are present in certain embodiments include one or more polymer initiators, dyes, cross-linking agents, catalysts, or polymer-chain size modifiers. In some embodiments, combinations of additional components are added to the prepolymer mixture. The quantities and identities of such components can be readily determined by one skilled in the art based on the desired properties of the resulting foam, Although certain prepolymers and structural features of the non-denatured collagens or additives listed below may in some cases also act as polymer initiators, dyes, cross-linking agents, catalysts, or polymer-chain-size modifiers, for the purpose of this patent, these components when claimed separately are defined to be distinct from the prepolymers, additives, and non-denatured collagens present in the mixtures.

In some embodiments of the invention, superabsorbent polymers are added for controlled release of the dispersed additives or the collagen or to modify the water-absorbing or water-releasing properties of the foam. Suitable superabsorbent polymers and their characteristics can be found for example in U.S. Pat. Nos. 5,763,335 and 4,914,470, hereby incorporated by reference in their entirety. In general, superabsorbents are considered to be water-insoluble materials which are capable of absorbing and retaining large amounts of water or other aqueous fluids in relation to their own weight. In some industrial applications, compounds are considered to be superabsorbent when they can absorb at least fifteen tunes their own weight of aqueous fluids.

The at least one additive in some embodiments of this invention is selected from a group consisting of skin care agents, hydrocolloid absorptive agents, medicaments, proteins, enzymes, nucleic acids, vitamins, soaps, hemostatic agents, antibacterial agents, antifungal agents, surfactants, pH buffers, mineral salts, trace elements, plant extracts, animal extracts, disinfecting and sterilizing agents, and combinations thereof.

The non-denatured collagen in some embodiments of this invention is prepared by a process which does not disrupt the fibrillar structure of the natural collagen. Without intending to be bound to a single theory, it can be noted that in general terms, the following description of collagen is widely accepted. Natural collagen is the most abundant protein found in mammals and is the main component of fibrous connective tissue such as skin, tendons, and ligaments. There are several forms of collagen found in the body with different macromolecular structures, but over 90% of the collagen is a fibrous structural form known as Type I collagen. This consists of protein chain subunits with a relatively high proportion of glycine, proline, and hydroxyproline each polypeptide strand forming a left-handed helix. Three of these subunits are twisted together to form a right-handed triple helix "super-coil" stabilized by numerous hydrogen bonds. These triple-helices further combine to form a right-handed "super-super-coil" called a collagen microfibril, which are further stabilized by the presence of some covalent cross-linking. Multiple microfibrils associate to form tropocollagen, which is a fibril approximately 300 nm long and 1.5 nm, in diameter. These tropocollagens spontaneously self assemble into larger fibrillar structures which are further stabilized by additional covalent cross-linking between tropocollagen subunits. Still larger fibrillar bundles are formed with the aid of several different classes of proteins, glycoproteins, and proteoglycans to form insoluble collagen which composes different types of mature tissue.

Collagen can be isolated from these mature tissues by several processes, many of which denature the fibrillar structure of the collagen to a greater or lesser extent. Strong acids or bases and high temperatures irreversibly hydrolyze the covalent bonding between peptide strands, leading to gelatin, or even further to degrade the protein strands themselves and yield a soup of amino acid residues. Strictly mechanical processes can be used to isolate the collagen fibrils in a more or less pure form from tissues such as calf tendon which contain less mature collagen structures and relatively few contaminating proteins.

For the purposes of this application, a non-denatured collagen is defined as natural collagen extracted from tissue by a process which leaves the fibrillar bundles relatively intact but which substantially removes extraneous tissues, fats, and proteins. Such collagen has not been solubilized by acid is or basic treatments and is largely insoluble. We have found that these non-denatured collagens have different properties from the denatured and solubilized collagen products resulting from treatment with strong acids and bases, and are uniquely suitable for several cosmetic sponge applications.

In some embodiments, this non-denatured collagen is formed by carefully controlling the pH and amount of heat to which the collagen is exposed during the extraction process. By avoiding extremes of pH and heat, the denaturation, or bass of natural structure, of the collagen is avoided or at least minimized. One method for preparing a suitable collagen from bovine skin has been described in Brazilian patents PI09029915 and PI0203122, hereby incorporated by reference in their entirety. In these processes, the skin from healthy cattle, is treated to remove muscles and fat from the inner layer of the skin, and calcined with calcium hydroxide to allow the separation of the skin into an exodermis and endodermis. The endodermis is then treated with dilute acetic acid or dilute hydrochloric acid at only moderately low pH for de-calcination, pressed between sanitary rubber rollers in a drier to remove excess water, then milled to form a slurry and dried with very short times in a drum dryer (120-170°C. for 30-45 seconds) or at lower temperatures in a static bed (50-90° C. for 3 to 10 hours). Treatment by particle breaker, cutting mill, and hammer mill followed by hand-screening produce a substantially sterile, uniform product having fiber lengths less than 10 mm and advantageously between 3 and 5 mm, fat content less than 7%, moisture content less than 30%, and protein content between 70 and 95%. By maintaining a relatively narrow range of pH and relatively low temperatures, the collagen fibrils are denatured as little as possible during the isolation process. The upper limit of pH of the process is maintained between approximately 8 and approximately 13, and the lower limit of pH is maintained between approximately 3 and approximately 5, more neutral pH being associated with less denaturization of the protein. It has been found that this method of isolating collagen involving a combination of chemical and mechanical processing characterized by careful control of pH and temperature not only provides a less denatured collagen product than previous chemical methods, with more of the elasticity and structural characteristics of the natural collagen, but also provides a cleaner and purer product than the previous mechanical processes.

We have found the properties of non-denatured collagen prepared under these conditions to be uniquely suitable for use in the current invention. Collagen prepared under conditions in which the pH is maintained between 3 and 13 forms fibers of suitable length, radius, and elasticity to be of benefit to the skin and to add firmness to the resulting sponge, while collagen formed under conditions in which those pH ranges are exceeded loses most of its fibrous structure to form a gelatinous, soluble material. In some embodiments, the collagen is prepared under still narrower pH conditions of between 4 and 10 resulting in thicker and stiffer collagen fibrils which contribute elasticity and still more firmness to the resulting sponge. In some embodiments, a stiffer, stronger collagen is prepared using conditions of pH between 5 and 9, and the resulting sponge is also stronger and stiffer without losing the resilience and elasticity of non-denatured collagen. Even this narrower pH range is sufficient to remove the undesired proteins, fats, and other biological substances which would be present in, collagen treated only at neutral pH or by strictly mechanical processes, while leaving the fibril structure of the natural collagen intact. These differing forms of non-denatured collagen can be mixed with each other in appropriate proportions to modify the properties of the resulting sponge.

In some embodiments, the polymer foam is a hydrophilic urethane foam. Hydrophilic urethane prepolymers are available in the commercial marketplace, for example, those sold under the trademark BIPOL 6 by Mace Adhesives and Coatings, under the trademark HYPOL by The Dow Chemical Company, or under the trademark PREPOL by Lendall Manufacturing Incorporated. General procedures for the preparation and formation of such prepolymers can be found in Polyurethane's Chemistry and Technology by J. H. Saunders and K. C. Frisch published by John Wiley & Sons, New York, N.Y., at Vol. XVI Part 2. High Polymer Series, "Foam systems",Pages 7-26, and "Procedures for the Preparation of Polymers" pages 26 et. seq. Admixing an aqueous mixture with a predetermined amount of the hydrophilic urethane prepolymer initiates polymerization. The physical characteristics of the resulting polymer foam, such as density and tensile strength, are controlled by the ratio of prepolymer in the aqueous mixture.

In some embodiments, one or more agents including cross-linking agents, catalysts, or surfactants are added to the mixture to further modify the physical characteristics of the resulting polymer foam. Cross-linking agents are small multifunctional compounds that, under the appropriate reaction conditions, form additional covalently bonded cross-links between segments of the polymer. In some embodiments these additional crosslinks increase the stiffness, strength or toughness of the resulting foam. In some embodiments they are used to link the collagen or the additives to the matrix of the polymer foam through covalent bonds. In some embodiments they are used to add desirable functionality to the resulting foam such as color, hydrophilicity, visible or ultraviolet light resistance or sensitivity, and resistance to oxidative degradation.

Catalysts are materials which are used to modify the reaction rate of the polymerization reaction. In some embodiments, they are added to promote the polymerization reaction under specific conditions of air, heat or light activation, allowing control of such variables as pot life and reaction temperature of the prepolymer mixture, and cell formation, number, and size in the resulting foam. Some catalysts suitable for use in polyurethane systems include those sold under the trademark BiCAT by Shepherd Chemical Company and those sold under the trademarks DABCO and POLYCAT by Air Products.

Surfactants are compounds which are added to increase the solubility of other materials in the aqueous prepolymer mixture. In one embodiment, a surfactant is added as part of the, aqueous collagen mixture. In another embodiment, a surfactant is added as part of an aqueous solution of other agents or additives prepared before addition to the prepolymer mixture. In some embodiments, the surfactants are present in amounts of about 0.5% to about 5% by weight of the aqueous mixture. A wide variety of anionic, cationic, non-ionic, and zwitterionic surfactants are commercially available, and the choice of surfactant can be readily determined by one skilled in the art based on the nature of the materials to be dissolved. In some embodiments, surfactants are used to modify the resulting polymer foam by controlling the number or size of the cells, and in some embodiments the incorporation of the surfactant in the polymer matrix is used to modify the hydrophilicity of the resulting foam.

Figure 2:
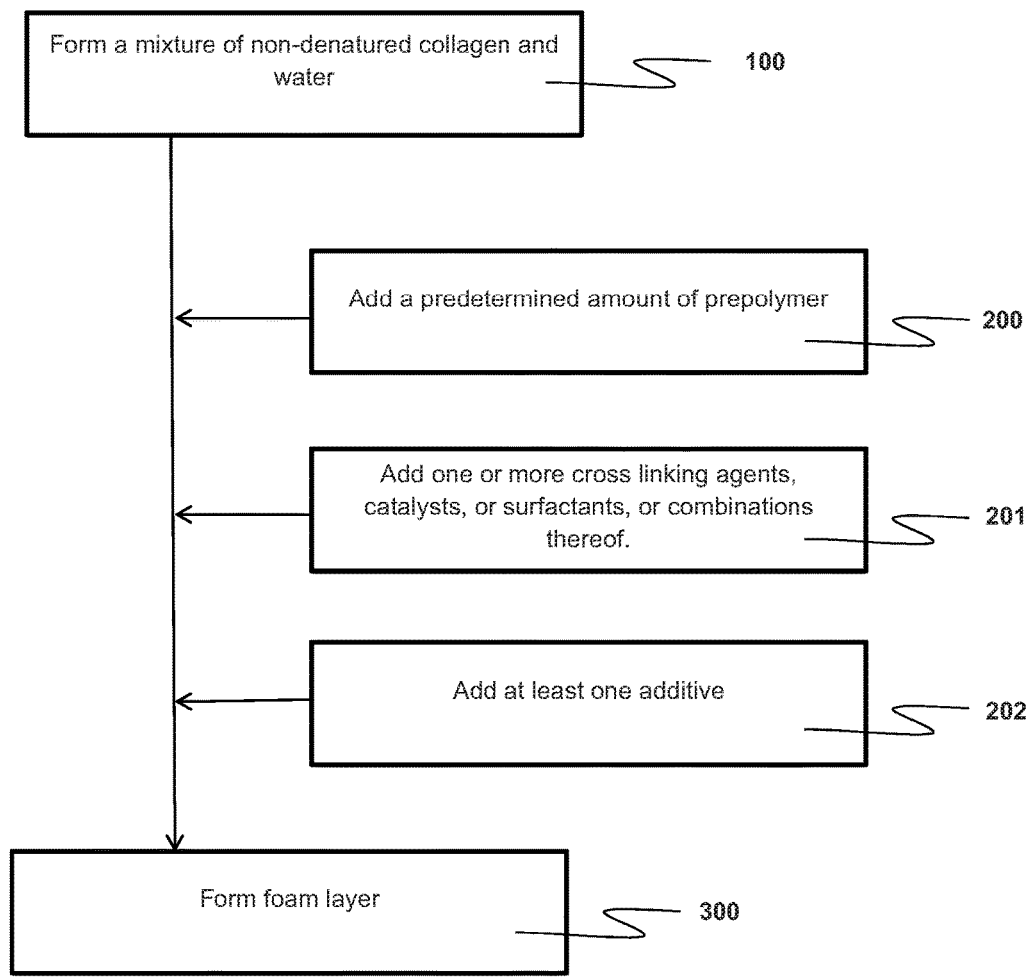
FIG. 2 is a flowchart depicting one embodiment of a method for providing the cosmetic sponge shown in FIG. 1.

FIG. 2 depicts another embodiment of this invention; a method for providing a cosmetic sponge comprising the steps of forming a mixture having at least a predetermined amount of non-denatured collagen and water (100), and mixing a predetermined amount of prepolymer with said mixture (200), forming a prepolymer mixture which polymerizes to form a foam layer (300).

In some embodiments, the predetermined amount of prepolymer is chosen based on the handling characteristics of the resulting prepolymer mixture. In many embodiments, this amount ranges from about 10% by weight to about 50% by weight of the prepolymer mixture. In some embodiments, the predetermined amount of the non-denatured collagen is chosen based on the desired properties and expected use of the resulting foam. In many embodiments, this amount ranges from between about 1% by weight to about 25% by weight of the mixture. In some embodiments, the invention comprises the additional step of adding one or more agents selected from a group consisting of a cross-linking agent, a catalyst, a surfactant, and combinations thereof (201). In different embodiments, these agents are incorporated into the mixture of non-denatured collagen and water, incorporated into the prepolymer, or added separately. In some embodiments, the invention comprises the additional step of adding at least one additive from the group consisting of skin care agents, hydrocolloid absorptive agents, medicaments, proteins, enzymes, nucleic acids, vitamins, soaps, hemostatic agents, antibacterial agents, antifungal agents, surfactants, pH buffers, mineral salts, trace elements, plant extracts, animal extracts, disinfecting and sterilizing agents, and combinations thereof (202). The order of addition of the various components does not form a part of this invention, and can be selected or changed without exceeding the intended scope of the invention by those skilled in the art, based on considerations such as the solubility of the components in the mixture, chemical stability, or ease of manufacturing.

Figure 3:
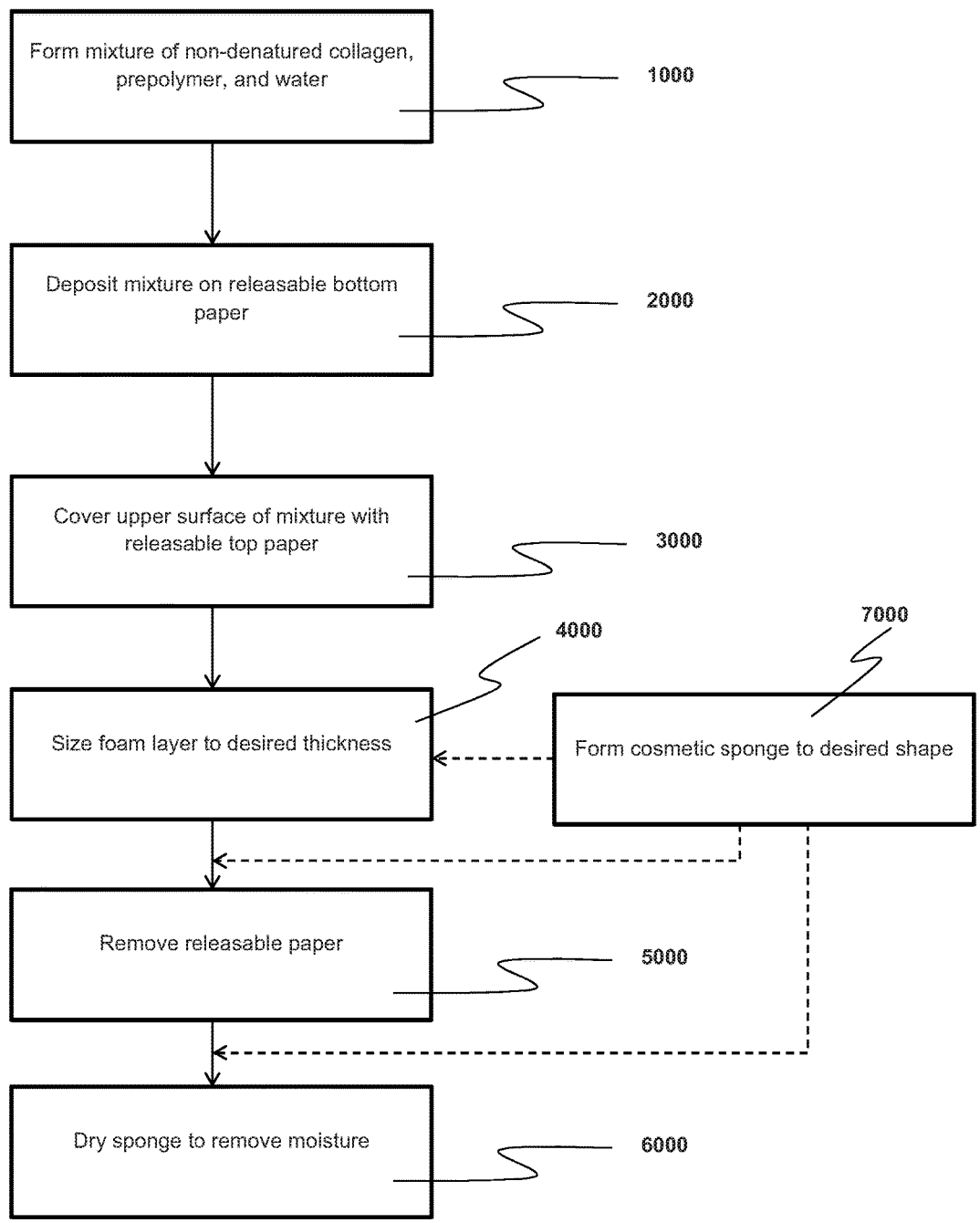
FIG. 3 is a flowchart depicting a second embodiment of a method for providing the cosmetic sponge shown in FIG. 1.

FIG. 3 depicts an embodiment of the present invention in which a method is provided for forming a cosmetic sponge comprising the steps of forming an aqueous mixture having at least a predetermined amount of non-denatured collagen, a predetermined amount of prepolymer, and an adequate amount of water (1000); depositing the mixture on releasable bottom paper (2000); covering the upper surface of the mixture with releasable top paper (3000); sizing the foam layer to the desired thickness (4000); removing the top and bottom releasable paper (5000); and either simultaneously or subsequently drying the sized cosmetic sponge to remove moisture (6000). In some embodiments the releasable bottom paper is disposed on a movable carrier. In some embodiments, the foam layer, effectively contained between releasable papers, is advanced between steps of the process, by moving the carrier. In some embodiments the cosmetic sponge is formed to the de d shape as it is sized (7000); in other embodiments, the sponge is formed as a separate step either before or after removing the releasable papers and drying the foam.

Figure 4:
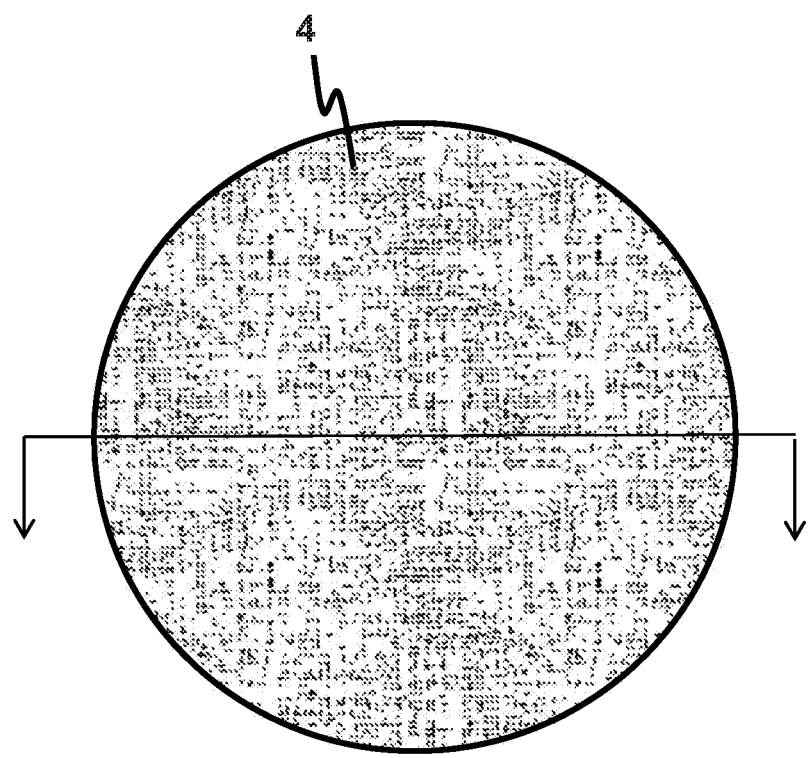
FIG. 4 depicts an embodiment of the cosmetic sponge shown in FIG. 1 with a cover layer in accordance with the present invention.
Figure 4A:
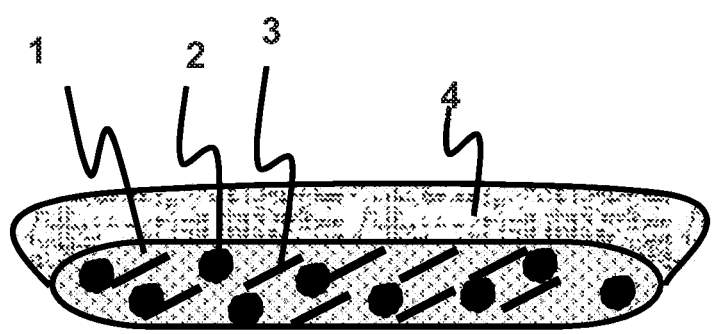
FIG. 4a depicts the same embodiment in cutaway view, to show the internal structure of the sponge.

In some embodiments of the invention, the cosmetic sponge is composed of more than one layer. Such layered composite materials reflect in part the teachings of U.S. Pat. Nos. 5,763,335 and 6,025,287, which are hereby incorporated by reference in their entirety. FIGS. 4 and 4a depict an embodiment of the present invention in which the cosmetic sponge is a layered composite material comprising a polymer foam (1) containing a non-denatured collagen (2) and at least one additive (3), in contact with a cover layer (4) of a second material. This contact between the polymer foam and the cover layer allows water and any additives present in the foam layer to be carried through into the cover layer to the skin, and allows water and any solutes on the skin to be carried through the cover layer and into the underlying foam.

In some embodiments, the cosmetic sponge is covered by, and in some embodiments, bonded to, an additional layer of differing composition. In some embodiments, a cover layer of material less hydrophilic than the underlying polymer foam is provided. This allows water to be absorbed by the polymer foam and water soluble additives to be released from the foam and onto the cover layer, while leaving the cover layer dry enough to act as an applicator for cosmetics or for the absorbed additives. In other embodiments, a cover layer more hydrophilic than the underlying polymer foam is provided. This allows especially hydrophilic additives to be more readily transferred to the cover layer for application. In other embodiments, the cover layer has similar properties to the underlying foam, differing in physical properties such as softness, pore size, or abrasiveness, to allow for two different surfaces of differing characteristics for applying cosmetics. In some embodiments, the cover layer is similar to the underlying foam layer but includes a different additive or combination of additives.

In one embodiment, the cover layer is formed of randomized polyester fiber material dispensed from a roll onto the upper surface of the polymer foam. Randomized fiber materials are materials in which the fibers are not aligned throughout the material. In some embodiments, the fibers are aligned in two or more different directions in adjoining portions of the material. In some embodiments, the fibers are aligned in different directions for different layers of the material. In some embodiments, the randomized fiber materials consist of non-oriented or randomly oriented fiber materials, materials in which the fibers are not oriented in any particular direction and for which the direction of any fiber within the material appears random.

The composite material is formed by joining the cover layer to the polymer foam by any suitable means. In one embodiment, the foam and cover layer are joined by needle punching which forces certain of the polyester fibers into and sometimes through the foam to establish the composite material. When needle punching is used to connect the cover layer to the foam layer, the fibers forming the cover layer are reduced to a generally non-measurable thickness, impart a fabric feel to the top surface of the formed composite material, and act as a wick to distribute and transfer moisture or bodily fluids from the cover layer to the hydrophilic foam layer.

Other materials are used as cover layers to impart different properties to the composite foam material, and in different embodiments the material used as a cover layer is selected from randomized acrylic fiber material, sock liner material, thermoformable acrylic latex non-woven fiber web, or non-woven felted web materials. In different embodiments, the cover layer is attached to the foam by different means including adhesives, radio frequency heating, flame bonding, or by directly polymerizing the foam layer onto the cover layer.

Figure 5:
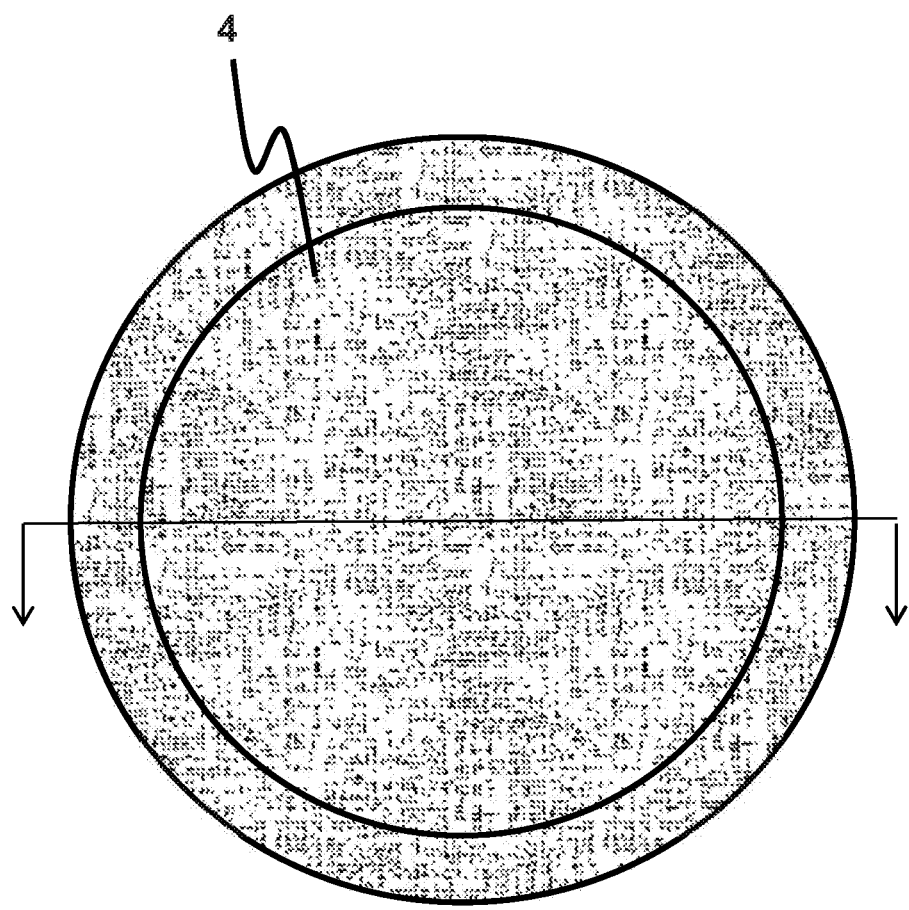
FIG. 5 depicts an embodiment of the cosmetic sponge shown in FIG. 1 with a cover layer and a third layer, in accordance with the present invention.
Figure 5A:
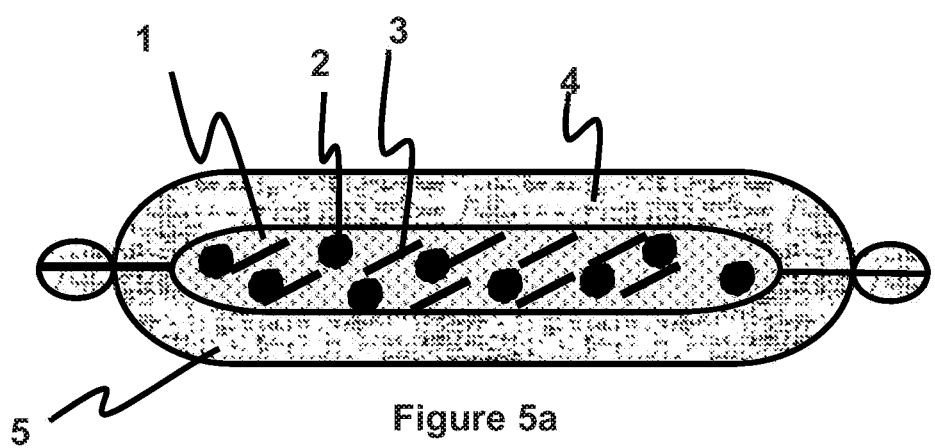
FIG. 5a depicts the same embodiment in cutaway view, to show the internal structure of the sponge.

FIGS. 5 and 5a depict an embodiment of the present invention comprising a polymer foam (1) containing a non-denatured collagen (2) and at least one additive (3), a cover layer in contact with a first surface of said foam (4), and a third layer in contact with a second surface of said foam (5). In some embodiments the cover layer and third layer are bonded to the polymer foam; in other embodiments, the cover layer and third layer are bonded together outside the periphery of the polymer foam, such that the cover layer and third layer together surround and enclose the polymer foam. Like the cover layer, the third layer may be more hydrophilic, less hydrophilic, or of similar characteristics to the underlying polymer foam, and in some embodiments contains the same, and in ether embodiments contains different additives from the polymer foam.

In some embodiments, the corer layer and if present the third layer, comprise a material selected from the group consisting of a randomized polyester fiber material, a sock liner material, a non-woven material, a non-woven fiber web, and a felted non-woven fiber web.

While the present invention has been particularly described it is evident that many alternatives, modifications and variations will be apparent to those skilled in the art in light of the foregoing description. It is therefore contemplated that the appended claims will embrace any such alternative, modifications, and variations as falling within the true scope and spirit of the present invention.

What is claimed is:

1. A cosmetic sponge comprising a polymer foam, a non-denatured collagen, and at least one additive, and wherein the non-denatured collagen further includes a fat content less than approximately 7%.

2. The cosmetic sponge of claim 1, wherein the non-denatured collagen further includes a moisture content less than approximately 30%.

3. The cosmetic sponge of claim 1 wherein the non-denatured collagen is prepared under pH conditions ranging from approximately 13 to approximately 3.

4. The cosmetic sponge of claim 1 wherein the non-denatured collagen is prepared under pH conditions ranging from approximately 9 to approximately 5.

5. The cosmetic sponge of claim 1 wherein the at least one additive is selected from the group consisting of: skin care agents, hydrocolloid absorptive agents, medicaments, proteins, enzymes, nucleic acids, vitamins, soaps, hemostatic agents, antibacterial agents, antifungal agents, surfactants, pH buffers, mineral salts, trace elements, plant extracts, animal extracts, disinfecting and sterilizing agents, and combinations thereof.

6. The cosmetic sponge of claim 1, wherein the sponge is a reaction product of a mixture comprising:
   a predetermined amount of non-denatured collagen; a predetermined amount of a prepolymer; and at least one additive.

7. The cosmetic sponge of claim 6, wherein the amount of prepolymer is between approximately 10% and approximately 50% by weight.

8. The cosmetic sponge of claim 6, wherein the amount of non-denatured collagen is between approximately 1% and approximately 25% by weight.

9. The cosmetic sponge of claim 1 further comprising an agent from the group consisting of: a cross-linking agent, a catalyst, a surfactant, and combinations thereof.

10. The cosmetic sponge of claim 1, wherein the non-denatured collagen further includes a fiber length less than approximately 10 mm.

11. A cosmetic sponge comprising a polymer foam, a non-denatured collagen, and at least one additive, and wherein the non-denatured collagen further includes a protein content between approximately 70% and approximately 95%.

12. The cosmetic sponge of claim 11 wherein the non-denatured collagen is prepared under pH conditions ranging from approximately 13 to approximately 3.

13. The cosmetic sponge of claim 11 wherein the non-denatured collagen is prepared under pH conditions ranging from approximately 9 to approximately 5.

14. The cosmetic sponge of claim 11 wherein the at least one additive is selected from the group consisting of: skin care agents, hydrocolloid absorptive agents, medicaments, proteins, enzymes, nucleic acids, vitamins, soaps, hemostatic agents, antibacterial agents, antifungal agents, surfactants, pH buffers, mineral salts, trace elements, plant extracts, animal extracts, disinfecting and sterilizing agents, and combinations thereof.

15. The cosmetic sponge of claim 11, wherein the sponge is a reaction product of a mixture comprising:
   a predetermined amount of non-denatured collagen; a predetermined amount of a prepolymer; and at least one additive.

16. The cosmetic sponge of claim 15, wherein the amount of prepolymer is between approximately 10% and approximately 50% by weight.

17. The cosmetic sponge of claim 15, wherein the amount of non-denatured collagen is between approximately 1% and approximately 25% by weight.

18. The cosmetic sponge of claim 11 further comprising an agent from the group consisting of: a cross-linking agent, a catalyst, a surfactant, and combinations thereof.

19. The cosmetic sponge of claim 11, wherein the non-denatured collagen further includes a fiber length less than approximately 10 mm.

20. The cosmetic sponge of claim 11, wherein the non-denatured collagen further includes a moisture content less than approximately 30%.

\* \* \* \* \*